(12) United States Patent
Dransfield et al.

(10) Patent No.: US 7,503,970 B2
(45) Date of Patent: Mar. 17, 2009

(54) PARTICULATE METAL OXIDE

(75) Inventors: Graham Paul Dransfield, Stockton on Tees (GB); Susan Cutter, Middlesbrough (GB); Phillip Laurence Lyth, Stockton on Tees (GB)

(73) Assignee: Croda International PLC, East Yorkshire (GB)

( * ) Notice: Subject to any disclaimer, the term of this patent is extended or adjusted under 35 U.S.C. 154(b) by 0 days.

(21) Appl. No.: 11/783,993

(22) Filed: Apr. 13, 2007

(65) Prior Publication Data
US 2007/0191497 A1 Aug. 16, 2007

Related U.S. Application Data

(60) Continuation of application No. 11/266,214, filed on Nov. 4, 2005, now Pat. No. 7,220,305, which is a division of application No. 10/324,082, filed on Dec. 20, 2002, now Pat. No. 7,101,427, which is a continuation of application No. PCT/GB01/02781, filed on Jun. 25, 2001.

(30) Foreign Application Priority Data

| Jun. 26, 2000 | (GB) | 0015381.7 |
| Jun. 25, 2001 | (WO) | GB01/02781 |

(51) Int. Cl.
C04B 14/00 (2006.01)
C04B 14/04 (2006.01)
C09C 1/04 (2006.01)
C09C 1/14 (2006.01)
C09C 1/36 (2006.01)
C09C 1/10 (2006.01)
C09C 1/34 (2006.01)
C09C 1/22 (2006.01)
C09C 1/02 (2006.01)
C08K 3/00 (2006.01)
C08K 5/00 (2006.01)
A61K 8/18 (2006.01)
B32B 5/16 (2006.01)
B32B 9/00 (2006.01)
B32B 15/02 (2006.01)
B32B 17/02 (2006.01)
B32B 19/00 (2006.01)
B32B 21/02 (2006.01)
B32B 23/02 (2006.01)
B32B 27/02 (2006.01)

(52) U.S. Cl. ........... 106/401; 106/419; 106/426; 106/429; 106/432; 106/442; 106/443; 106/447; 106/450; 106/452; 106/453; 106/455; 106/456; 106/460; 106/461; 106/471; 106/479; 106/480; 106/482; 106/490; 106/491; 424/59; 428/403

(58) Field of Classification Search ........... 106/401, 106/419, 425, 429, 432, 442, 443, 447, 450, 106/455, 452, 453, 460, 461, 456, 471, 479, 106/480, 482, 491, 499; 424/59; 428/403
See application file for complete search history.

(56) References Cited

U.S. PATENT DOCUMENTS

| 4,246,040 A | 1/1981 | Okumura et al. |
| 4,851,293 A | 7/1989 | Egerton et al. |
| 4,927,464 A | 5/1990 | Cowie |
| 5,068,056 A * | 11/1991 | Robb ............ 516/90 |
| 5,336,521 A | 8/1994 | Dransfield et al. |
| 5,573,753 A | 11/1996 | Tapley |
| 5,599,529 A * | 2/1997 | Cowie ............ 424/59 |
| 5,846,310 A * | 12/1998 | Noguchi et al. ...... 106/482 |
| 5,891,237 A | 4/1999 | Kinniard |
| 5,914,101 A | 6/1999 | Tapley et al. |
| 6,132,739 A | 10/2000 | Leverett |
| 6,267,949 B1 | 7/2001 | Halls |
| 6,534,044 B1 | 3/2003 | Wada et al. |
| 6,683,130 B2 | 1/2004 | Kessell |
| 6,846,479 B2 | 1/2005 | Lorant et al. |
| 6,855,311 B2 | 2/2005 | Lennon et al. |
| 7,101,427 B2 * | 9/2006 | Dransfield et al. ....... 106/401 |
| 7,220,305 B2 * | 5/2007 | Dransfield et al. ....... 106/401 |
| 2003/0223940 A1 * | 12/2003 | Dransfield et al. ....... 424/59 |
| 2005/0069706 A1 * | 3/2005 | Kessell .............. 428/403 |
| 2006/0228310 A1 * | 10/2006 | Lyth ................. 424/59 |
| 2008/0008757 A1 * | 1/2008 | Kessell et al. ........ 424/486 |
| 2008/0044483 A1 * | 2/2008 | Kessell ............. 424/498 |
| 2008/0057008 A1 * | 3/2008 | Naden et al. .......... 424/59 |

FOREIGN PATENT DOCUMENTS

| EP | 0599492 | 6/1994 |
| EP | 0861806 | 9/1998 |
| GB | 2205088 | 11/1988 |
| GB | 2206339 | 1/1989 |
| GB | 2226018 | 6/1990 |
| JP | 62 197463 | 9/1987 |

* cited by examiner

*Primary Examiner*—Patricia L Hailey
(74) *Attorney, Agent, or Firm*—Jones Day

(57) ABSTRACT

A particulate metal oxide having the mean length of the primary particles in the range from 50 to 90 nm, the mean width of the primary particles in the range from 5 to 20 nm, and the median volume particle diameter of the secondary particles is less than 45 nm. The metal oxide can be used in a sunscreen product that exhibits both effective UV protection and improved transparency.

30 Claims, No Drawings

PARTICULATE METAL OXIDE

CROSS REFERENCE TO RELATED APPLICATION

This application is a Continuation Application of U.S. Ser. No. 11/266,214, filed Nov. 4, 2005, which is a Divisional of U.S. Ser. No. 10/324,082, filed Dec. 20, 2002, which is a continuation of International Application No. PCT/GB2001/002781, filed Jun. 25, 2001. These applications, in their entirety, are incorporated herein by reference.

FIELD OF INVENTION

The present invention relates to a particulate metal oxide, a metal oxide dispersion and in particular to the use thereof in a sunscreen product.

BACKGROUND OF THE INVENTION

Metal oxides such as titanium dioxide, zinc oxide and iron oxides have been employed as attenuators of ultraviolet light in applications such as sunscreens, plastics films and resins. Due to the increased awareness of the link between ultraviolet light and skin cancer, there has been an increasing requirement for ultraviolet light protection in everyday skincare and cosmetics products. Unfortunately, existing commercially available metal oxide products, such as titanium dioxide, are not sufficiently transparent and can have an unacceptable whitening effect when used on the skin. There is a need for a metal oxide which exhibits improved transparency, reduced whitening, and provides broad spectrum ultraviolet light protection,

REVIEW OF THE PRIOR ART

GB-2206339-A is directed to an oil dispersion of titanium dioxide particles having a particle size in the range from 0.01 to 0.15 microns. GB-2205088-A discloses particulate acicular titanium dioxide having a coating layer of aluminium oxide and silicon oxide.

GB-2226018-A is directed to an aqueous dispersion of particulate acicular titanium dioxide containing an acrylic dispersing agent.

SUMMARY OF THE INVENTION

We have now surprisingly discovered an improved metal oxide, which overcomes or significantly reduces at least one of the aforementioned problems.

Accordingly, the present invention provides a particulate metal oxide wherein the mean length of the primary particles is in the range from 50 to 90 nm, the mean width of the primary particles is in the range from 5 to 20 nm, and the median particle volume diameter of the secondary particles is less than 45 nm.

The present invention also provides a dispersion comprising particles of metal oxide in a dispersing medium wherein the mean length of the primary particles is in the range from 50 to 90 nm, the mean width of the primary particles is in the range from 5 to 20 nm, and the median particle volume diameter of the secondary particles is less than 45 nm.

The invention further provides a particulate metal oxide wherein the mean length of the primary particles is in the range from 55 to 85 nm, the mean width of the primary particles is in the range from 8 to 19 nm, and at least 70% of the primary particles have a length in the range from 55 to 85 nm.

The invention further provides a particulate metal oxide, optionally hydrophobic, having an extinction coefficient at 524 nm ($E_{524}$) in the range from 0.2 to 0.7 l/g/cm, an extinction coefficient at 450 nm ($E_{450}$) in the range from 0.5 to 1.5 l/g/cm, an extinction coefficient at 360 nm ($E_{360}$) in the range from 4 to 8 l/g/cm, an extinction coefficient at 308 nm ($E_{308}$) in the range from 40 to 60 l/g/cm, a maximum extinction coefficient E(max) in the range from 50 to 70 l/g/cm, and a $\lambda$(max) in the range from 270 to 290 nm.

The invention further provides a sunscreen product comprising a metal oxide or dispersion as defined herein.

The invention still further provides the use of a metal oxide or dispersion as defined herein in the manufacture of a sunscreen having reduced whiteness.

Preferably the metal oxide used in the present invention comprises an oxide of titanium, zinc or iron, and most preferably the metal oxide is titanium dioxide.

The preferred titanium dioxide particles comprise anatase and/or rutile crystal form. The titanium dioxide particles preferably comprise a major portion of rutile, more preferably greater than 60% by weight, particularly greater than 70%, and especially greater than 80% by weight of rutile. The titanium dioxide particles preferably comprise in the range from 0.01 to 5%, more preferably 0.1 to 2%, and particularly 0.2 to 0.5% by weight of anatase. In addition, the titanium dioxide particles preferably comprise less than 40%, more preferably less than 30%, and particularly less than 25% by weight of amorphous titanium dioxide. The basic particles may be prepared by standard procedures, such as using the chloride process, or by the sulphate process, or by hydrolysis of an appropriate titanium compound such as titanium oxydichloride or an organic or inorganic titanate, or by oxidation of an oxidisable titanium compound, e.g. in the vapour state. The titanium dioxide particles are preferably prepared by the hydrolysis of a titanium compound, particularly of titanium oxydichloride.

The individual or primary metal oxide particles are preferably acicular in shape and have a long axis (maximum dimension or length) and short axis (minimum dimension or width). The third axis of the particles (or depth) is preferably approximately the same dimensions as the width. The size of the primary particles can be suitably measured using electron microscopy. The size of a particle can be determined by measuring the length and width of a filler particle selected from a photographic image obtained by using a transmission electron microscope. Mean values can be determined from the measurements of at least 300 particles, as described herein.

The mean length by number of the primary metal oxide particles is. in the range from 50 to 90 nm, preferably 55 to 85 nm, more preferably 60 to 80 nm, particularly 65 to 77 nm, and especially 69 to 73 nm. The mean width by number of the particles is in the range from 5 to 20 nm, preferably 8 to 19 nm, more preferably 10 to 18 nm, particularly 12 to 17 nm, and especially 14 to 16 nm.

The size distribution of the primary metal oxide particles can also have a significant effect on the final properties of, for example, a sunscreen product comprising the metal oxide. In a preferred embodiment of the invention suitably at least 40%, preferably at least 50%, more preferably at least 60%, particularly at least 70%, and especially at least 80% by number of particles have a length within the above preferred ranges given for the mean length. In addition, suitably at least 40%, preferably at least 50%, more preferably at least 60%, particularly at least 70%, and especially at least 80% by number of particles have a width within the above preferred ranges given for the mean width.

The primary metal oxide particles preferably have a mean aspect ratio $d_1:d_2$ (where $d_1$ and $d_2$, respectively, are the length and width of the particle) in the range from 2.0 to 8.0:1, more preferably 3.0 to 6.5:1, particularly 4.0 to 6.0:1, and especially 4.5 to 5.5:1.

The primary metal oxide particles preferably have a median volume particle diameter (equivalent spherical diameter corresponding to 50% of the volume of all the particles, read on the cumulative distribution curve relating volume % to the diameter of the particles—often referred to as the "D(v,0.5)" value), measured as herein described, in the range from 25 to 35 nm, more preferably 27 to 33 nm, particularly 28 to 32 nm, and especially 29 to 31 nm.

In one embodiment of the invention, the primary metal oxide particles aggregate to form clusters or agglomerates of secondary particles comprising a plurality of metal oxide primary particles. The aggregation process of the primary metal oxide particles may take place during the actual synthesis of the metal oxide and/or during subsequent processing. The mean number of primary metal oxide particles present in the secondary particles according to the present invention is suitably in the range from 1 to 10, preferably 1.05 to 8, more preferably 1.1 to 5, particularly 1.3 to 3, and especially 1.4 to 2.0. Thus, statistically at least some of the secondary particles may contain only one primary particle, i.e. some primary particles are also secondary particles. The term "secondary" particles is partly used as a label to relate to particle size results obtained using a particular technique, as described herein.

The particulate metal oxide according to the present invention has a median volume particle diameter (equivalent spherical diameter corresponding to 50% of the volume of all the particles, read on the cumulative distribution curve relating volume % to the diameter of the particles—often referred to as the "D(v,0.5)" value)) of the secondary particles, measured as herein described, of less than 45 nm, preferably in the range from 30 to 40 nm, more preferably 32 to 38 nm, particularly 33 to 37 nm, and especially 34 to 36 nm.

The size distribution of the secondary metal oxide particles can also be an important parameter in obtaining, for example, a sunscreen product having the required properties. The metal oxide particles preferably have no more than 16% by volume of particles having a volume diameter of less than 20 nm, more preferably less than 24 nm, particularly less than 28 nm, and especially less than 32 nm. In addition, the metal oxide particles preferably have more than 84% by volume of particles having a volume diameter of less than 70 nm, more preferably less than 60 nm, particularly less than 50 nm, and especially less than 40 nm.

It is preferred that none of the secondary metal oxide particles should have an actual particle size exceeding 150 nm. Particles exceeding such a size may be removed by milling processes which are known in the art. However, milling operations are not always totally successful in eliminating all particles greater than a chosen size. In practice, therefore, the size of 95%, preferably 99% by volume of the particles should not exceed 150 nm.

Particle size of the secondary metal oxide particles described herein may be measured by electron microscope, coulter counter, sedimentation analysis and static or dynamic light scattering. Techniques based on sedimentation analysis are preferred. The median particle size may be determined by plotting a cumulative distribution curve representing the percentage of particle volume below chosen particle sizes and measuring the 50th percentile. The median particle volume diameter of the secondary metal oxide particles is suitably measured using a Brookhaven particle sizer, as described herein.

In a particularly preferred embodiment of the invention, the metal oxide particles have a BET specific surface area, measured as described herein, of greater than 40, more preferably in the range from 50 to 100, particularly 60 to 90, and especially 65 to 75 $m^2/g$.

The particles of metal oxide may comprise substantially pure metal oxide, but in one embodiment of the invention the particles have an inorganic coating. For example, metal oxide particles, such as titanium dioxide, may be coated with oxides of other elements such as oxides of aluminium, zirconium or silicon, or mixtures thereof such as alumina and silica as disclosed in GB-2205088-A, the teaching of which is incorporated herein by reference. The preferred amount of inorganic coating is in the range from 2% to 25%, more preferably 4% to 20%, particularly 6% to 15%, and especially 8% to 12% by weight, calculated with respect to the weight of metal oxide core particles. The inorganic coating may be applied using techniques known in the art. A typical process comprises forming an aqueous dispersion of metal oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate.

In a particularly preferred embodiment of the invention, the particles of metal oxide are coated in order to render them hydrophobic. Suitable coating materials are water-repellent, preferably organic, and include fatty acids, preferably fatty acids containing 10 to 20 carbon atoms, such as lauric acid, stearic acid and isostearic acid, salts of the above fatty acids such as sodium salts and aluminium salts, fatty alcohols, such as stearyl alcohol , and silicones such as polydimethylsiloxane and substituted polydimethylsiloxanes, and reactive silicones such as methylhydrosiloxane and polymers and copolymers thereof. Stearic acid and/or salt thereof is particularly preferred. The organic coating may be applied using any conventional process. Typically, metal oxide particles are dispersed in water and heated to a temperature in the range 50° C. to 80° C. A fatty acid, for example, is then deposited on the metal oxide particles by adding a salt of the fatty acid (e.g. sodium stearate) to the dispersion, followed by an acid. Alternatively, the metal oxide core particles can be mixed with a solution of the water-repellent material in an organic solvent, followed by evaporation of the solvent. In an alternative embodiment of the invention, the water-repellant material can be added directly to the dispersion, during preparation thereof, such that the hydrophobic coating is formed in situ. Generally, the particles are treated with up to 25%, more preferably in the range from 3% to 20%, particularly 6% to 17%, and especially 10% to 15% by weight of organic material, preferably fatty acid, calculated with respect to the metal oxide core particles.

In a preferred embodiment of the invention, the metal oxide particles may be coated with both an inorganic and an organic coating, either sequentially or as a mixture. It is preferred that the inorganic coating, preferably alumina, is applied first followed by the organic coating, preferably fatty acid and/or salt thereof. Thus, preferred metal oxide particles according to the present invention comprise (i) in the range from 60% to 98%, more preferably 65% to 95%, particularly 70% to 80%, and especially 72% to 78% by weight of metal oxide, preferably titanium dioxide, with respect to the total weight of the particles, (ii) in the range from 0.5% to 15%, more preferably 2% to 12%, particularly 5% to 10%, and especially 6% to 9% by weight of inorganic coating, preferably alumina, with respect to the total weight of the particles, and (iii) in the range from 1% to 21%, more preferably 4% to 18%, particularly 7% to 15%, and especially 9% to 12% by weight of organic coating, preferably fatty acid and/or salt thereof, with respect to the total weight of the particles. Such metal oxide particles provide a surprising combination of both improved photostability and dispersibility, particularly when dispersed in a suitable organic medium.

The metal oxide particles used in the present invention exhibit improved transparency preferably having an extinction coefficient at 524 nm ($E_{524}$), measured as herein described, of less than 2.0, more preferably in the range from 0.1 to 1.0, particularly 0.2 to 0.7, and especially 0.3 to 0.5 l/g/cm. In addition, the metal oxide particles preferably have an extinction coefficient at 450 nm ($E_{450}$), measured as herein described, of less than 3.0, more preferably in the range from 0.1 to 2.0, particularly 0.5 to 1.5, and especially 0.7 to 1.0 l/g/cm. The metal oxide particles exhibit effective UV absorption, suitably having an extinction coefficient at 360 nm ($E_{360}$), measured as herein described, of greater than 3, preferably in the range from 4 to 10, more preferably 5 to 8, particularly 5.5 to 7.5, and especially 6 to 7 l/g/cm.

The metal oxide particles also preferably having an extinction coefficient at 308 nm ($E_{308}$), measured as herein described, of greater than 30, more preferably in the range from 35 to 65, particularly 40 to 60, and especially 45 to 55 l/g/cm.

The metal oxide particles preferably have a maximum extinction coefficient E(max), measured as herein described, in the range from 40 to 80, more preferably from 45 to 75', particularly 50 to 70, and especially 55 to 65 l/g/cm. The metal oxide particles preferably have a λ(max), measured as herein described, in the range from 260 to 290, more preferably −265 to 285, particularly 268 to 280, and especially 270 to 275 nm.

The metal oxide particles suitably exhibit reduced whiteness, preferably having a change in whiteness ΔL of a sunscreen product containing the particles, measured as herein described, of less than 3, more preferably in the range from 0.5 to 2.5, and particularly 1.0 to 2.0.. In addition, a sunscreen product containing the particles preferably has a whiteness index, measured as herein described, of less than 100%, more preferably in the range from 10% to 80%, particularly 20% to 60%, and especially 30% to 50%.

The metal oxide particles suitably have reduced photogreying, preferably having a photogreying index, measured as herein described, of less than 15, more preferably in the range from 1 to 10, particularly 2 to 7, and especially 3 to 5. The particulate metal oxide according to the present invention may be in the form of a free-flowing powder. A powder having the required particle size for the secondary metal oxide particles, as described herein, may be produced by milling processes known in the art. The final milling stage of the metal oxide is suitably carried out in dry, gas-borne conditions to reduce aggregation. A fluid energy mill can be used in which the aggregated metal oxide powder is continuously injected into highly turbulent conditions in a confined chamber where multiple, high energy collisions occur with the walls of the chamber and/or between the aggregates. The milled powder is then carried into a cyclone and/or bag filter for recovery. The fluid used in the energy mill may be any gas, cold or heated, or superheated dry steam.

The particulate metal oxide may be formed into a slurry, or preferably a liquid dispersion, in any suitable aqueous or organic liquid medium. By liquid dispersion is meant a true dispersion, i.e., where the solid particles are stable to aggregation. The particles in the dispersion are relatively uniformly dispersed and resistant to settling out on standing, but if some settling out does occur, the particles can be easily redispersed by simple agitation. Cosmetically acceptable materials are preferred as the liquid medium. A useful organic medium is a liquid oil such as vegetable oils, e.g. fatty acid glycerides, fatty acid esters and fatty alcohols. A preferred organic medium is a siloxane fluid, especially a cyclic oligomeric dialkylsiloxane, such as the cyclic pentamer of dimethylsiloxane known as cyclomethicone. Alternative fluids include dimethylsiloxane linear oligomers or polymers having a suitable fluidity and phenyltris(trimethylsiloxy)silane (also known as phenyltrimethicone).

Examples of suitable organic media include avocado oil, C12-15 alkyl benzoate, C12-15 alkyl ethylhexanoate, C12-15 alkyl lactate, C12-15 alkyl salicylate, C13-14 isoparaffin, C18-36 acid glycol ester, C18-36 acid triglyceride, caprylic/capric glycerides, caprylic/capric triglyceride, caprylic/capric/lauric triglyceride, caprylic/capric/linoleic triglyceride, caprylic/capric/myristic/stearic triglyceride, caprylic/capric/stearic triglyceride, castor oil, castor oil-silicone ester, cetearyl ethylhexanoate, cetearyl isononanoate, cetearyl palmitate, cetearyl stearate, cetyl dimethicone, cetyl dimethicone copolyol, cetyl ethylhexanoate, cetyl glycol isostearate, cetyl isononanoate, cetyl lactate, cetyl myristate, cetyl oleate, cetyl palmitate, cetyl ricinoleate, cetyl stearate, cocoglycerides, coconut oil, cyclomethicone, cyclopentasiloxane, cyclotetrasiloxane, decyl isostearate, decyl oleate, decyl polyglucoside, dibutyl adipate, diethylhexyl dimer dilinoleate, diethylhexyl malate, diisopropyl adipate, diisopropyl dimer dilinoleate, diisostearoyl trimethylolpropane siloxy silicate, diisostearyl adipate, diisostearyl dimer dilinoleate, di isostearyl malate, diisostearyl trimethylolpropane siloxy silicate, dilauroyl trimethylolpropane siloxy silicate, dilauryl trimethylolpropane siloxy silicate, dimethicone, dimethicone copolyol, dimethicone propyl PG-betaine, dimethiconol, dimethyl isosorbide, dioctyl maleate, dioctylodedecyl dimer dilinoleate, ethylhexyl benzoate, ethylhexyl cocoate, ethylhexyl dimethyl PABA, ethylhexyl ethylhexanoate, ethylhexyl hydroxystearate, ethylhexyl hydroxystearate benzoate, ethylhexyl isononanoate, ethylhexyl isopalmitate, ethylhexyl isostearate, ethylhexyl laurate, ethylhexyl methoxycinnamate, ethylhexyl myristate, ethylhexyl neopentanoate, ethylhexyl oleate, ethylhexyl palmitate, ethylhexyl salicylate, ethylhexyl stearate, glyceryl caprate, glyceryl caprylate, glyceryl caprylate/caprate, glyceryl cocoate, glyceryl dilaurate, glyceryl dioleate, glyceryl hydroxystearate, glyceryl isostearate, glyceryl laurate, glyceryl oleate, glycol oleate, glycol ricinoleate, helianthus annuus (hybrid sunflower) seed oil, helianthus annuus (sunflower) seed oil, homosalate, isoamyl laurate, isoamyl p-methoxycinnamate, isocetyl alcohol, isocetyl behenate, isocetyl ethylhexanoate, isocetyl isostearate, isocetyl laurate, isocetyl linoleoyl stearate, isocetyl myristate, isoce tyl palmitate, isocetyl salicylate ,isocetyl stearate, isocetyl stearoyl stearate, isohexadecane, isononyl isononanoate, isopropyl C12-15-pareth-9 carboxylate, isopropyl isostearate, isopropyl lanolate, isopropyl laurate, isopropyl linoleate, isopropyl methoxycinnamate, isopropyl myristate, isopropyl oleate, isopropyl palmitate, isopropyl PPG-2-isodeceth-7 carboxylate, isopropyl ricinoleate, isopropyl stearate, isostearic acid, isostearyl alcohol, isostearyl ethylhexanoate, isostearyl isononanoate, isostearyl isostearate, isostearyl lactate, isostearyl myristate, isostearyl neopentanoate, isostearyl palmitate, isostearyl stearoyl stearate, jojoba oil, lanolin (lanolin oil), maleated soybean oil, mnyristyl isostearate, myristyl lactate, myristyl myristate, myristyl neopentanoate, myristyl stearate, octocrylene, octyldecanol, octyldodecanol, oenothera biennis (evening primrose oil), paraffinum liquidum (mineral oil), PCA dimethicone, pentaerythrityl tetraisononanoate, pentaerythrityl tetraisostearate, perfluropolymethylisopropyl ether, persea gratissima (avocado oil), phenyl trimethicone, PPG-15 stearyl ether, propylene glycol ceteth-3 acetate, propylene glycol dicaprylate, propylene glycol dicaprylate/dicaprate, propylene glycol dipelargonate, propylene glycol distearate, propylene glycol isoceteth-3 acetate, propylene glycol isostearate, propylene glycol laurate, proylene glycol ricinoleate, propylene glycol stearate, prunus dulcis (sweet almond oil), squalane, squalene, tricaprylin, tricaprylyl citrate, tridecyl ethylhexanoate, tridecyl neopentanoate, tridecyl stearoyl stearate, triethylhexanoin, triethylhexyl citrate, trihydroxystearin, triisocetyl citrate, triisostearin, triisostearyl citrate, trimethylolpropane triisostearate, trimethylsiloxysilicate, triticum vulgare (wheat germ oil), vitis vinifera (grape) seed oil, and mixtures thereof.

The metal oxide dispersions may also contain a dispersing agent in order to improve the properties thereof. The dispersing agent is preferably present in the range from 1% to 50%, more preferably 3% to 30%, particularly 5% to 20%, and especially 8% to 15% by weight based on the total weight of metal oxide particles.

Suitable dispersing agents for use in an organic medium include substituted carboxylic acids, soap bases and polyhydroxy acids. Typically the dispersing agent can be one having a formula X.CO.AR in which A is a divalent bridging group, R is a primary secondary or tertiary amnino group or a salt thereof with an acid or a quaternary ammonium . salt group and X is the residue of a polyester chain which together with the —CO— group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxystearic acid small amounts of stearic acid and palmitic acid. Dispersing agents based on one or more polyesters or salts of a hydroxycarboxylic acid and a carboxylic acid free of hydroxy groups can also be used. Compounds of various molecular weights can be used. Other suitable dispersing agents are those monoesters of fatty acid alkanolamides and carboxylic acids and their salts. Alkanolamides are based on ethanolamine, propanolamine or aminoethyl ethanolamine for example. Alternative dispersing agents are those based on polymers or copolymers of acrylic or methacrylic acids, e.g. block copolymers of such monomers. Other dispersing agents of similar general form are those having epoxy groups in the constituent radicals such as those based on the ethoxylated phosphate esters. The dispersing agent can be one of those commercially referred to as a hyper dispersant. Suitable dispersing agents for use in an aqueous medium include a polymeric acrylic acid or a salt thereof. Partially or fully neutralized salts are usable e.g. the alkali metal salts and ammonium salts. Examples of dispersing agents are polyacrylic acids, substituted acrylic acid polymers, acrylic copolymers, sodium and/or ammonium salts of polyacrylic acids and sodium and/or ammonium salts of acrylic copolymers. Such dispersing agents are typified by polyacrylic acid itself and sodium or ammonium salts thereof as well as copolymers of an acrylic acid with other suitable monomers such as a sulphonic acid derivative such as 2-acrylamido 2-methyl propane sulphonic acid. Comonomers polymerisable with the acrylic or a substituted acrylic acid can also be one containing a carboxyl grouping. Usually the dispersing agents have a molecular weight of from 1,000 to 10,000 and are substantially linear molecules.

A surprising feature of the present invention is that dispersions, particularly in an organic medium, can be produced which contain at least 35%, preferably at least 40%, more preferably at least 45%, particularly at least 50%, especially at least 55%, and generally up to 60% by weight of the total weight of the dispersion, of metal oxide particles.

Alternatively, the particulate metal oxide may be in the form of a lotion or cream of a solid and/or semi-solid dispersion. Suitable solid or semi-solid dispersions may contain, for example, in the range from 50% to 90%, preferably 60% to 85% by weight of particulate metal oxide according to the present invention, together with any one or more of the liquid media disclosed herein, or a high molecular polymeric material, such as a wax.

The particulate metal oxide and dispersions of the present invention are useful as ingredients for preparing sunscreen compositions, especially in the form of emulsions. The dispersion may further contain conventional additives suitable for use in the intended application, such as conventional cosmetic ingredients used in sunscreens. The particulate metal oxide according to the present invention may provide the only ultraviolet light attenuators in a sunscreen product according to the invention, but other sunscreen agents, such as other metal oxides and/or other organic materials may also be added. For example, the preferred titanium dioxide particles described herein may be used in combination with existing commercially available titanium dioxide and/or zinc oxide sunscreens. Suitable organic sunscreens for use with metal oxide according to the invention include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, and 4-methylbenzylidene camphor.

The invention is illustrated by the following non-limiting examples. In this specification, the following test methods have been used to determine certain properties of the metal oxide particles:

1) Particle Size Measurement of Primary Metal Oxide Particles

A small amount of metal oxide, typically 2 mg, was pressed into approximately 2 drops of an oil, for one or two minutes using the tip of a steel spatula. The resultant suspension was diluted with solvent and a carbon-coated grid suitable for transmission electron microscopy was wetted with the suspension and dried on a hot-plate. Approximately 18 cm×21 cm photographs were produced at an appropriate, accurate magnification. Generally about 300-500 crystals were displayed at about 2 diameters spacing. A minimum number of 300 primary particles were sized using a transparent size grid consisting of a row of circles of gradually increasing diameter, representing spherical crystals. Under each circle a series of ellipsoid outlines were drawn representing spheroids of equal volume and gradually increasing eccentricity. The basic method assumes log normal distribution standard deviations in the 1.2-1.6 range (wider crystal size distributions would require many more crystals to be counted, for example of the order of 1000). The dispersion method described above has been found to be suitable for producing almost totally dispersed distributions of primary metal oxide particles whilst introducing minimal crystal fracture. Any residual aggregates (or secondary particles) are sufficiently well defined that they, and any small debris, can be ignored, and effectively only primary particles included in the count.

Mean length, mean width and length/width size distributions of the primary metal oxide particles can be calculated from the above measurements. Similarly, the median particle volume diameter of the primary particles can also be calculated.

2) Median Particle Volume Diameter Measurement of Secondary Metal Oxide Particles A dispersion of metal oxide particles was produced by mixing 10 g of polyhydroxystearic acid with 90 g of isopropyl myristate, and then adding 100 g of metal oxide into the solution. The mixture was passed through a horizontal bead mill, operating at approximately 1500 r.p.m. and containing zirconia beads as grinding media for 15 minutes. The dispersion of metal oxide particles was diluted to between 30 and 40 g/l by mixing with isopropyl myristate. The diluted sample was analyzed on the Brookhaven BI-XDC particle sizer in centrifugation mode, and the median particle volume diameter measured.

3) BET Specific Surface Area of Metal Oxide Particles

The single point BET specific surface area was measured using a Micromeritics Flowsorb II 2300.

4) Change in Whiteness and Whiteness Index

A sunscreen formulation was coated on to the surface of a glossy black card and drawn down using a No 2 K bar to form a film of 12 µm wet thickness. The film was allowed to dry at room temperature for 10 minutes and the whiteness of the coating on the black surface ($L_F$) measured using a Minolta CR300 colourimeter. The change in whiteness $\Delta L$ was calculated by subtracting the whiteness of the substrate ($L_S$) from the whiteness of the coating ($L_F$). The whiteness index is the percentage change in whiteness $\Delta L$ compared to a standard titanium dioxide (=100% value) (Tayca MT100T (ex Tayca Corporation)).

5) Photogreying Index

A metal oxide dispersion was placed inside a 6 cm×3 cm acrylic cell (containing a 2 cm×1.5 cm space), and the cell made air tight by clamping a glass slide over the top, ensuring that no air bubbles were present. The initial whiteness ($L_I$) was measured using a Minolta CR300 colourimeter. The cell was then placed on a turntable revolving at 30 rpm and exposed to UV light for 2 hours (a UV lamp containing 4 TL29D,16/09 tubes mounted 12 cm from the cell), and the whiteness ($L_T$) remeasured. The photogreying index $\Delta L = L_I - L_T$.

EXAMPLES

Example 1

2 moles of titanium oxydichloride in acidic solution were reacted with 6 moles of NaOH in aqueous solution, with stirring, in a 3 liter glass vessel. After the initial reaction phase, the temperature was increased to above 70° C., by heating at a rate of approximately 1° C./min, and tirring continued for at least another 60 minutes. The mixture was then neutralised by the addition of NaOH in aqueous solution, and allowed to cool below 70° C.

To the resultant dispersion, an alkaline solution of sodium aluminate was added, equivalent to 7% by weight $Al_2O_3$ on $TiO_2$ weight. The temperature was maintained below 70° C. during the addition. The temperature was then increased to above 70° C., and stirred for at least another 10 minutes. Sodium stearate equivalent to 12.5% by weight stearate on weight of $TiO_2$ was added, and the reaction mixture again stirred for at least a further 10 minutes.

The dispersion was neutralised to pH 6.5 to 7.0 by adding 36% hydrochloric acid solution over 30 minutes. The neutralised slurry was aged for 15 minutes whilst being stirred. The slurry was then filtered to produce a filter cake which was then washed repeatedly with demineralised water until the cake conductivity (when a small sample was reslurried to 100 g/l) was less than 500 □s. The filter cake was dried in an oven at 105° C. for 16 hours and then micropulverised using a hammer mill to produce particulate titanium dioxide.

A dispersion was produced by mixing 10 g of polyhydroxystearic acid with 90 g of isopropyl myristate, and then adding 100 g of the titanium dioxide produced above into the solution. The mixture was passed through a horizontal bead mill, operating at approximately 1500 r.p.m. and containing zirconia beads as grinding media for 15 minutes.

The dispersion was subjected to the test procedures described herein, and the titanium dioxide exhibited the following properties:

Primary Particles
i) Mean length=71 nm,
ii) Mean width=15.2 nm,
iii) Mean aspect ratio=4.7,
iv) Number of particles having a length within 55 to 85 nm=79% and
v) D(v,0.5)=30 nm.

Secondary Particles
i) D (v,0.5)=35 nm,
ii) 16% by volume of particles have volume diameter less than 27 nm,
iii) 84% by volume of particles have volume diameter less than 46 nm,
iv) BET specific surface area 70 m²/g, and
v) Photogreying index=7.

A sample (0.1 g) of the milled titanium dioxide dispersion produced above was diluted with cyclohexane (100 ml). This diluted sample was then further diluted with cyclohexane in the ratio sample:cyclohexane of 1:19. The total dilution was 1:20,000. The diluted sample was then placed in a spectrophotometer (Perkin-Elmer Lambda 2 UVNIS Spectrophotometer) with a 1 cm path length and the absorbance, of UV and visible light measured. Extinction coefficients were calculated from the equation A=E.c.l, where A=absorbance, E=extinction coefficient in liters per gram per cm, c=concentration in grams per liter, and l=path length in cm.

The results were as follows:

| $E_{524}$ | $E_{450}$ | $E_{308}$ | $E_{360}$ | E(max) | λ(max) |
|---|---|---|---|---|---|
| 0.4 | 0.9 | 43.4 | 5.6 | 64.7 | 273 |

Example 2

This titanium dioxide dispersion produced in Example 1 was used to prepare a sunscreen formulation having the following composition.

|  | % by weight |
|---|---|
| Phase A: | |
| Arlacel P135 (ex Uniqema) | 2.0 |
| Arlamol HD P135 (ex Uniqema) | 5.0 |
| AEC Cyclomethicone (Pentamer) (ex A&E Connock Ltd) | 5.6 |
| Jojoba Oil) (ex A&E Connock Ltd) | 4.0 |
| Arlamol E (ex Uniqema) | 2.4 |
| Candelilla Wax (ex Eggar&Co Chemicals Ltd) | 1.0 |
| Magnesium Stearate | 0.7 |
| Titanium Dioxide dispersion produced above | 12.0 |
| Phase B: | |
| Allantoin (ex Uniqema) | 0.2 |
| Atlas G-2330 (ex Uniqema) | 3.0 |
| D-Panthenol (EX Roche Products Ltd) | 0.8 |
| Magnesium Sulfate | 0.7 |
| Aqua (Water) | 61.6 |
| Preservative | 1.0 |

The ingredients of phase A were mixed and heated to 75-80° C. The ingredients of phase B were mixed and heated to 75-80° C. and slowly added to phase A with intensive mixing, followed by stirring with a Silverson mixer for 2 minutes. Finally, the mixture was cooled with intensive stirring.

The change in whiteness ΔL was 1.84, and the whiteness index was 600%, for the above sunscreen product. The Sun Protection Factor of the sunscreen product was determined using the in vitro method of Diffey and Robson, J. Soc. Cosmet. Chem. Vol. 40, pp 127-133, 1989, and a value of 10.7 was obtained.

Example 3

The procedure of Example 1 was repeated except that the micropulverised particulate titanium dioxide was mixed at a concentration of 100 g/l with 9:1 isopropyl myristate/polyhydroxystearic acid, and milled with 150 μm glass beads (Ballotini Grade II) in a small scale sand mill. The resultant titanium dioxide dispersion had the following extinction coefficient values:

| $E_{524}$ | $E_{450}$ | $E_{308}$ | $E_{360}$ | E(max) | λ(max) |
|---|---|---|---|---|---|
| 0.2 | 0.6 | 41.8 | 4.7 | 62.1 | 274 |

The above examples illustrate the improved properties of a particulate metal oxide, dispersion and sunscreen product according to the present invention.

The invention claimed is:

1. A dispersion comprising coated metal oxide particles in a dispersing medium, said metal oxide particles having secondary particles, wherein the median particle volume diameter of the secondary particles is less than 45 nm, and more than 84% by volume of the secondary particles have a volume diameter of less than 60 nm, wherein the metal oxide particles have an extinction coefficient at 524 nm ($E_{524}$) of less than 2.0 l/g/cm and an extinction coefficient at 308 nm ($E_{308}$) in the range from 40 to 65 l/g/cm.

2. A dispersion according to claim 1 wherein more than 84% by volume of the secondary particles have a volume diameter of less than 50 nm.

3. A dispersion according to claim 1 wherein no more than 16% by volume of the secondary particles have a volume diameter of less than 20 nm.

4. A dispersion according to claim 3 wherein no more than 16% by volume of the secondary particles have a volume diameter of less than 24 nm.

5. A dispersion according to claim 1 wherein the median particle volume diameter of the secondary particles is in the range from 30 to 40 nm.

6. A dispersion according to claim 5 wherein the median particle volume diameter of the secondary particles is 30 to 38 nm.

7. A dispersion according to claim 6 wherein the median particle volume diameter of the secondary particles is 30 to 36 nm.

8. A dispersion according to claim 1 wherein the metal oxide particles are hydrophobic.

9. A dispersion according to claim 8 wherein the metal oxide particles comprise an organic water repellant coating.

10. A dispersion according to claim 1 wherein the metal oxide particles comprise (i) in the range from 65% to 95% by weight of titanium dioxide, (ii) in the range from 2% to 12% by weight of inorganic coating, and (iii) in the range from 4% to 18% by weight of organic coating, all with respect to the total weight of the metal oxide particles.

11. A dispersion according to claim 1 comprising at least 35% by weight of metal oxide particles.

12. A dispersion according to claim 11 comprising at least 40% by weight of metal oxide particles.

13. A dispersion according to claim 12 comprising at least 45% by weight of metal oxide particles.

14. A dispersion according to claim 1 wherein the dispersing medium is a cosmetically acceptable liquid organic medium.

15. A dispersion according to claim 1 wherein the dispersing medium is an aqueous medium.

16. A dispersion according to claim 1 wherein the metal oxide is titanium dioxide.

17. A dispersion according to claim 1 comprising in the range from 3 to 30% by weight of a dispersing agent based on the total weight of the metal oxide particles.

18. A dispersion according to claim 1, wherein the metal oxide particles have an extinction coefficient at 524 nm ($E_{524}$) in the range from 0.1 to 1.0 l/g/cm.

19. A dispersion according to claim 1, wherein the metal oxide particles have an extinction coefficient at 308 nm ($E_{308}$) of 40 to 60 l/g/cm.

20. A dispersion according to claim 1 wherein the metal oxide particles are coated with an inorganic and/or organic coating.

21. A sunscreen product formed from or comprising a dispersion comprising coated metal oxide particles in a dispersing medium, said metal oxide particles having secondary particles, wherein the median particle volume diameter of the secondary particles is less than 45 nm, and more than 84% by volume of the secondary particles have a volume diameter of less than 60 nm, wherein the metal oxide particles have an extinction coefficient at 524 nm ($E_{524}$) of less than 2.0 l/g/cm and an extinction coefficient at 308 nm ($E_{308}$) in the range from 40 to 65 l/g/cm.

22. A sunscreen product according to claim 21 which is transparent when applied to the skin and has a change in whiteness ΔL in the range from 0.5 to 2.5.

23. A sunscreen product according to claim 21 having a whiteness index in the range from 10% to 80%.

24. A coated particulate metal oxide having secondary particles, wherein the median particle volume diameter of the secondary particles is less than 45 nm, and more than 84% by volume of the secondary particles have a volume diameter of less than 60 nm, wherein the particulate metal oxide has an extinction coefficient at 524 nm ($E_{524}$) of less than 2.0 l/g/cm and an extinction coefficient at 308 nm ($E_{308}$) in the range from 40 to 65 l/g/cm.

25. A dispersion comprising coated metal oxide particles in a dispersing medium, said coated metal oxide particles having secondary particles, wherein the median particle volume diameter of the secondary particles is less than 45 nm, no more than 16% by volume of the secondary particles have a volume diameter of less than 20 nm, and more than 84% by volume of the secondary particles have a volume diameter of less than 60 nm, wherein the metal oxide particles have an extinction coefficient at 524 nm ($E_{524}$) of less than 2.0 l/g/cm and an extinction coefficient at 308 nm ($E_{308}$) in the range from 40 to 65 l/g/cm.

26. The dispersion of claim 25, wherein the metal oxide particles have an extinction coefficient at 308 nm ($E_{308}$) of 40 to 60 l/g/cm.

27. The dispersion of claim 26, wherein the metal oxide particles have an extinction coefficient at 524 nm ($E_{524}$) in the range from 0.1 to 1.0 l/g/cm.

28. A dispersion comprising coated metal oxide particles in a dispersing medium, said coated metal oxide particles having secondary particles, wherein the secondary particles have a median particle volume diameter of less than 45 nm, wherein at least 68% by volume of the secondary particles have a volume diameter of 20-60 nm, wherein no more than 16% by volume of the secondary particles have a volume diameter of less than 20 nm, and wherein less than 16% by volume of the secondary particles have a volume diameter of more than 60 nm, wherein the metal oxide particles have an extinction coefficient at 524 nm ($E_{524}$) of less than 2.0 l/g/cm and an extinction coefficient at 308 nm ($E_{308}$) in the range from 40 to 65 l/g/cm.

29. The dispersion of claim 25, wherein the metal oxide particles have an extinction coefficient at 308 nm ($E_{308}$) of 40 to 60 l/g/cm 30. The dispersion of claim 25, wherein the dispersion has an extinction coefficient at 524 nm ($E_{524}$) in the range from 0.1 to 1.0 l/g/cm.

* * * * *